(12) United States Patent
Vaisnys et al.

(10) Patent No.: US 7,627,372 B2
(45) Date of Patent: Dec. 1, 2009

(54) SYSTEM AND METHOD FOR PRESENTING DEFIBRILLATOR STATUS INFORMATION WHILE IN STANDBY MODE

(75) Inventors: Gintaras A. Vaisnys, Guilford, CT (US); Glenn W. Laub, Guilford, CT (US); Giovanni C. Meier, Guilford, CT (US)

(73) Assignee: Defibtech, LLC, Princeton, NJ (US)

( * ) Notice: Subject to any disclaimer, the term of this patent is extended or adjusted under 35 U.S.C. 154(b) by 597 days.

(21) Appl. No.: 11/386,045

(22) Filed: Mar. 21, 2006

(65) Prior Publication Data

US 2006/0259080 A1 Nov. 16, 2006

Related U.S. Application Data

(60) Provisional application No. 60/663,908, filed on Mar. 21, 2005.

(51) Int. Cl.
*A61N 1/39* (2006.01)

(52) U.S. Cl. .......................................................... 607/5

(58) Field of Classification Search ...................... 607/5, 607/6, 8, 10, 16, 29; 600/522, 523; 128/898
See application file for complete search history.

(56) References Cited

U.S. PATENT DOCUMENTS

| | | |
|---|---|---|
| 4,101,787 A | 7/1978 | Vail |
| 4,590,943 A | 5/1986 | Paull et al. |
| 5,224,870 A | 7/1993 | Weaver et al. |
| 5,314,451 A | 5/1994 | Mulier |
| 5,350,317 A | 9/1994 | Weaver et al. |
| 5,372,605 A | 12/1994 | Adams et al. |
| 5,470,343 A | 11/1995 | Fincke et al. |
| 5,483,165 A | 1/1996 | Cameron et al. |
| 5,562,710 A | 10/1996 | Olsen et al. |
| 5,579,234 A | 11/1996 | Wiley et al. |
| 5,591,213 A | 1/1997 | Morgan et al. |
| 5,593,426 A | 1/1997 | Morgan et al. |
| 5,640,078 A | 6/1997 | Kou et al. |
| 5,645,571 A | 7/1997 | Olson et al. |
| 5,658,316 A | 8/1997 | Lamond et al. |

(Continued)

OTHER PUBLICATIONS

International Search Report dated Sep. 13, 2007 for International Application No. PCT/US06/10432.

(Continued)

*Primary Examiner*—Carl H Layno
*Assistant Examiner*—Elizabeth K So
(74) *Attorney, Agent, or Firm*—King & Spalding LLP

(57) ABSTRACT

A video display coupled to an automatic external defibrillator (AED) and capable of full-motion video can support added functionality of the AED. One advantage of the video display is that it can be used to present standby status information of the AED quickly to an AED operator while the AED is in a low power standby mode or non-operative state. The video display may present status information in response to touching the display or activating a button while the AED is in a non-operative state. When the AED is in an operative state, such as during a rescue, the display may comprise a graphical user interface that may be navigated using touch-screen technology or buttons built into the AED. During a rescue, the video display may present live or stored electrocardiograms (ECGs) and instructions for operating the AED.

26 Claims, 6 Drawing Sheets

U.S. PATENT DOCUMENTS

| | | | |
|---|---|---|---|
| 5,697,955 A | 12/1997 | Stolte | |
| 5,700,281 A | 12/1997 | Brewer et al. | |
| 5,721,482 A | 2/1998 | Benvegar et al. | |
| 5,741,305 A | 4/1998 | Vincent et al. | |
| 5,749,902 A | 5/1998 | Olson et al. | |
| 5,773,961 A | 6/1998 | Cameron et al. | |
| 5,782,878 A | 7/1998 | Morgan et al. | |
| 5,791,907 A | 8/1998 | Ramshaw et al. | |
| 5,792,190 A | 8/1998 | Olson et al. | |
| 5,797,969 A | 8/1998 | Olson et al. | |
| 5,800,460 A | 9/1998 | Powers et al. | |
| 5,817,151 A | 10/1998 | Olson et al. | |
| D405,754 S | 2/1999 | Barkley et al. | |
| 5,868,790 A | 2/1999 | Vincent et al. | |
| 5,868,794 A | 2/1999 | Barkley et al. | |
| 5,879,374 A | 3/1999 | Powers et al. | |
| 5,889,388 A | 3/1999 | Cameron et al. | |
| 5,897,576 A | 4/1999 | Olson et al. | |
| D409,752 S | 5/1999 | Bishay et al. | |
| 5,904,707 A | 5/1999 | Ochs et al. | |
| 5,913,685 A | 6/1999 | Hutchins | |
| 5,919,212 A | 7/1999 | Olson et al. | |
| 5,929,601 A | 7/1999 | Kaib et al. | |
| 5,944,741 A | 8/1999 | Ochs et al. | |
| 5,955,956 A | 9/1999 | Stendahl et al. | |
| 5,964,786 A | 10/1999 | Ochs et al. | |
| 5,983,137 A | 11/1999 | Yerkovich | |
| 5,999,493 A | 12/1999 | Olson | |
| 6,016,059 A | 1/2000 | Morgan | |
| 6,021,352 A | 2/2000 | Christopherson et al. | |
| 6,038,473 A | 3/2000 | Olson et al. | |
| 6,075,345 A | 6/2000 | Lee | |
| 6,101,413 A | 8/2000 | Olson et al. | |
| 6,128,530 A * | 10/2000 | Galen et al. | 607/5 |
| 6,141,584 A | 10/2000 | Rockwell et al. | |
| 6,148,233 A | 11/2000 | Owen et al. | |
| 6,152,754 A | 11/2000 | Gerhardt et al. | |
| 6,169,387 B1 | 1/2001 | Kaib | |
| 6,201,992 B1 | 3/2001 | Freeman | |
| 6,219,569 B1 | 4/2001 | Kelly et al. | |
| 6,230,053 B1 | 5/2001 | Magin | |
| 6,263,245 B1 | 7/2001 | Snell | |
| 6,278,366 B1 | 8/2001 | Fletcher et al. | |
| 6,301,502 B1 | 10/2001 | Owen et al. | |
| 6,304,780 B1 | 10/2001 | Owen et al. | |
| 6,314,320 B1 | 11/2001 | Powers et al. | |
| 6,334,070 B1 | 12/2001 | Nova et al. | |
| 6,363,282 B1 | 3/2002 | Nichols et al. | |
| 6,366,809 B1 | 4/2002 | Olson et al. | |
| 6,370,428 B1 | 4/2002 | Snyder et al. | |
| 6,374,137 B1 | 4/2002 | Morgan et al. | |
| 6,374,138 B1 | 4/2002 | Owen et al. | |
| 6,381,492 B1 | 4/2002 | Rockwell et al. | |
| 6,386,882 B1 | 5/2002 | Linberg | |
| 6,397,104 B1 | 5/2002 | Miller et al. | |
| 6,405,083 B1 | 6/2002 | Rockwell et al. | |
| 6,418,342 B1 | 7/2002 | Owen et al. | |
| 6,427,083 B1 | 7/2002 | Owen et al. | |
| 6,438,417 B1 | 8/2002 | Rockwell et al. | |
| 6,442,433 B1 | 8/2002 | Linberg | |
| 6,480,745 B2 | 11/2002 | Nelson | |
| 6,497,655 B1 | 12/2002 | Linberg et al. | |
| 6,546,285 B1 | 4/2003 | Owen et al. | |
| 6,586,850 B1 | 7/2003 | Powers | |
| 6,597,948 B1 | 7/2003 | Rockwell et al. | |
| 6,623,312 B2 | 9/2003 | Merry et al. | |
| 6,648,823 B2 | 11/2003 | Thompson | |
| 6,650,942 B2 | 11/2003 | Howard et al. | |
| 6,671,545 B2 | 12/2003 | Fincke | |
| 6,681,899 B1 | 1/2004 | Hong | |
| 6,697,671 B1 | 2/2004 | Nova et al. | |
| 6,754,538 B2 | 6/2004 | Linberg | |
| 6,799,072 B2 | 9/2004 | Ries et al. | |
| 6,820,998 B2 | 11/2004 | Chen | |
| 6,878,112 B2 | 4/2005 | Linberg et al. | |
| 6,920,360 B2 | 7/2005 | Lee et al. | |
| 6,944,498 B2 | 9/2005 | Owen et al. | |
| 6,955,864 B1 | 10/2005 | Vaisnys et al. | |
| 6,978,182 B2 | 12/2005 | Mazar et al. | |
| 6,990,371 B2 | 1/2006 | Powers et al. | |
| 6,993,386 B2 | 1/2006 | Lin et al. | |
| 2002/0032470 A1 | 3/2002 | Linberg et al. | |
| 2002/0082644 A1 | 6/2002 | Picardo et al. | |
| 2002/0095196 A1 | 7/2002 | Linberg et al. | |
| 2003/0004547 A1 | 1/2003 | Owen et al. | |
| 2003/0055460 A1 | 3/2003 | Owen et al. | |
| 2003/0068914 A1 | 4/2003 | Merry et al. | |
| 2003/0144711 A1 | 7/2003 | Pless et al. | |
| 2003/0205988 A1 | 11/2003 | Vaisnys et al. | |
| 2003/0216785 A1* | 11/2003 | Edwards et al. | 607/5 |
| 2004/0059405 A1 | 3/2004 | White et al. | |
| 2004/0122488 A1 | 6/2004 | Mazar et al. | |
| 2004/0133244 A1 | 7/2004 | Vaisnys et al. | |
| 2004/0143298 A1 | 7/2004 | Nova et al. | |
| 2004/0162586 A1 | 8/2004 | Covey et al. | |
| 2004/0215246 A1 | 10/2004 | Powers et al. | |
| 2004/0215278 A1 | 10/2004 | Stegink et al. | |
| 2005/0015115 A1 | 1/2005 | Sullivan et al. | |
| 2005/0036294 A1 | 2/2005 | McMahon | |
| 2005/0137653 A1 | 6/2005 | Friedman et al. | |
| 2005/0159787 A1 | 7/2005 | Linberg et al. | |
| 2005/0225983 A1 | 10/2005 | Fornell | |
| 2005/0261742 A1 | 11/2005 | Nova et al. | |

OTHER PUBLICATIONS

Heartstream.RTM., Fore Runner.RTM. Semi-Automatic Defibrillator User's Guide, pp. 6-9 and 50, no date.

Hewlett Packard, 43110 A Defibrillator/Monitor Operating Guide, Eighth Edition, pp. 2, 5,, 36-39, Aug. 1991.

Agilent Heartstream FR2, M3860A, M3861A, User's Guide, pp. 2-1-2-2, 2-4, 4-5, and B6, 2000.

Medtronic Physio-Control, Lifepack.RTM. 500 automated external defibrillator, Service Manual, pp. 3 of 12-4-12, 7 of 12-10 of 12, 12 of 12, 2001.

Medtronic Physio-Control, Lifepak.RTM. 500 Automated External Defibrillator Operating Instructions, pp. 2-5-2-6, 5-7-5-11, 5-16-5-17, Mar. 2001.

Survivalink FirstSave.TM. Operation and Service Manual, pp. 20, 29-31, 65, 70,84 and 85, 2000.

Swerdlow et al., "Cardiovascular Collapse Caused by Electrocardiographically Silent 60-Hz Intracardiac Leakage Current", 1999, American Heart Association, pp. 1-13.

* cited by examiner

SYSTEM AND METHOD FOR PRESENTING DEFIBRILLATOR STATUS INFORMATION WHILE IN STANDBY MODE

PRIORITY CLAIM TO PROVISIONAL APPLICATION

This application claims priority to provisional patent application entitled, "Defibrillator with Video Status Screen in Standby Mode" filed on Mar. 21, 2005 and assigned U.S. Application Ser. No. 60/663,908. The entire contents of the provisional patent application mentioned above are hereby incorporated by reference.

TECHNICAL FIELD

The present invention is generally directed to portable cardiac defibrillation systems with video displays, and relates more particularly to the use of video displays for supplying rapid standby status of a portable defibrillator through single-button activation while the defibrillator is in a non-operative state.

BACKGROUND OF THE INVENTION

Automatic external defibrillators (AEDs) are usually portable defibrillators that are designed to be operated by users with minimal training. AEDs are attached to a patient via electrode pads that allow an AED to send electrical shock energy to a patient for treating sudden cardiac arrest (SCA). Because AEDs can be used by non-medical personnel, they are being deployed in a myriad of locations outside of traditional medical settings. As a result, more and more non-medical establishments are purchasing portable AEDs for deployment in non-medical environments. To facilitate this deployment in various non-medical environments, portable AEDs are typically only powered by stand alone battery systems.

AEDs are usually standby devices that are used infrequently and that remain in storage for long periods of time. This standby storage time can be on the order of months or even years. Minimizing power consumed by the AED while it is in standby mode during storage may extend the battery life of the system and reserve battery power for rescue attempts using the AED.

Since AEDs are in standby mode for long periods of time, knowing the operational status of a standby AED is very important. The operational status of an AED can be determined by various internal self tests. These tests may cover general operations, battery life, memories, software, etc. The results of these tests can be communicated to a user via simple interfaces, such as light emitting diodes (LEDs), or via richer interfaces, such as video displays.

The operation of rich user interfaces, such as video displays, generally requires additional processing power from the main processor of the AED. However, fully powering up the entire AED device may unnecessarily consume significant electrical power relative to the shelf life of a portable AED. In addition to the problem of fully powering up the entire AED device, another problem exists with conventional AEDs that display status information only during the full power up of the AED.

Many conventional AEDs only provide status information prior to a rescue operation when the AED conducts self tests of its hardware, firmware, or software or any combination thereof. Conventional AEDs can also require a user to navigate through multiple menus in order to obtain status information about the AED.

For example, to obtain status information of conventional AEDs, a user usually must wait while the AED conducts internal self-tests prior to the AED being placed in a fully operational state. Once these internal self-tests are completed, the user usually must navigate through several menus on the AED in order to view status information. And if the user only desired status information of the AED without the need of powering up the AED into its fully operational state, then the user would also need to activate a switch on the AED in order to place the AED back into a non-operative state. Waiting to place an AED back into its non-operative state or standby mode can be a significant problem in situations in which numerous AEDs are checked in a series or close in time.

For example, a security guard making rounds in a multi-story building to check status of AEDs on each floor could encounter significant delays or waiting periods with conventional AEDs. That is, with conventional AEDs that require full power operation to perform self-tests, navigation through numerous menus to obtain status information, and that require the user to turn-off the AEDs once they reach their fully operative state could require a significant amount of time of a security guard who is patrolling the multi-story building.

Hence, there is a need in the art to provide rich status information, such as using a video display for presenting information about a portable AED and without consuming significant electrical power of the portable AED. There is also a need in the art for an AED that can provide rapid status information without requiring a user to navigate through complex or numerous menus. And a further need exists in the art for an AED that can provide status information without entering into a fully operational state and while the AED remains in a standby mode.

SUMMARY OF THE INVENTION

The inventive status indicating system may comprise a portable automatic external defibrillator (AED) with a video display that presents status information fairly quickly in response to a single button activation and without the AED entering into a fully operational state. That is, the inventive status indicating system of a portable AED may display status information on a video display while the AED is in a non-operative state and without requiring navigation through any complex menus and without requiring any self-tests of the AED. A non-operative state of the AED usually includes situations in which the AED is performing less than all of its primary functions. For example, a non-operative state usually includes situations in which an AED is not performing a rescue on a patient. Functions that may occur during non-operative states in AEDs may include self-tests and active status indicator events.

The video display may present status information with a graphical user interface while the AED is in the non-operative state. The status information may be presented upon activation of touch-screen technology or electromechanical inputs, such as buttons, built into the AED. When the AED is in a fully operational state, such as during a rescue, the video display may present live or stored electrocardiograms (ECGs).

The inventive system may comprise a low-power standby processor for monitoring user inputs, controlling status indicators, and determining when to power up the main processor of the AED. The standby processor can perform basic operations, such as monitoring user inputs and controlling status indicators without having to power up all of the system elements of the AED. Status indicators and the status video display may present information about the AED such as the results of internal tests, memory tests and battery status that are performed prior to activation of a status button or touch-screen technology.

When an operator requests the status of the AED, such as when a status button is activated by an operator, the AED may display status information on the video display. If the AED is in standby mode when the status display is requested by the operator, the low-power standby processor will activate the main processor only to display the status information on the video display and without causing the main processor to place the AED into a fully operational state. This activation of the main processor only to display status information, referred to as a standby status display, may conserve battery power of the AED system while still providing a rich video presentation of status information to the operator.

The inventive status indicating system may comprise a video display positioned within an AED. The video display may comprise any type of changeable visual presentation technology that is capable of displaying text or graphic (or both) output from a computer processor. For example, the video display may comprise liquid crystal display (LCD) technology, plasma displays, flat-screen display technology, three-dimensional or holographic technology, video projection technology, cathode ray tube (CRT) technology, and other similar display technology.

The display driver electronics, as well as the display itself, may provide for rapid update between images or frames so as to enable full-motion video when the AED is an fully operational state, such as during a rescue. A touch sensitive element may be positioned over, or incorporated within, the display as to enable touch-screen functionality for user inputs to the AED. Additionally, or in the alternative, user inputs may be accepted via buttons, switches, voice recognition, or other user input mechanisms known to one of ordinary skill in the art.

According to another alternate exemplary aspect, the inventive status indicating system can comprise a speaker for presenting oral or audible status information from a speaker in addition, or in the alternative, to presenting status information on a video display. Such embodiments would operate similar to the ones mentioned above: oral or audible status indication can be provided fairly rapidly while the AED is in a non-operative state in response to activation of a button, such as status button or an on/off power button.

DETAILED DESCRIPTION OF EXEMPLARY EMBODIMENTS

The inventive status indicating system may comprise an automatic external defibrillator (AED) with a built-in video display that presents status information without placing the AED into a fully operational state and in response to single button activation. The display driver electronics, as well as the display itself, may provide for rapid update between images or frames so as to enable full-motion video when the AED is in a fully operational state. The video display may be used to display patient ECGs, operator instructions, system status, training scenarios, or other information, video or user interface elements relevant to the functionality or use of the AED.

The inventive status indicating system may comprise a low power standby processor. The standby processor can react to operator inputs, power the main processor on and off to perform basic system status tests, power the main processor on and off for full operation of the AED, operate status indicators, and power the main processor for the purpose of only displaying a video status screen in certain situations. Performing these operations with the standby processor, which may be a very low power device, may conserve the AED's battery power and may extend battery life of the system.

Figure 1:
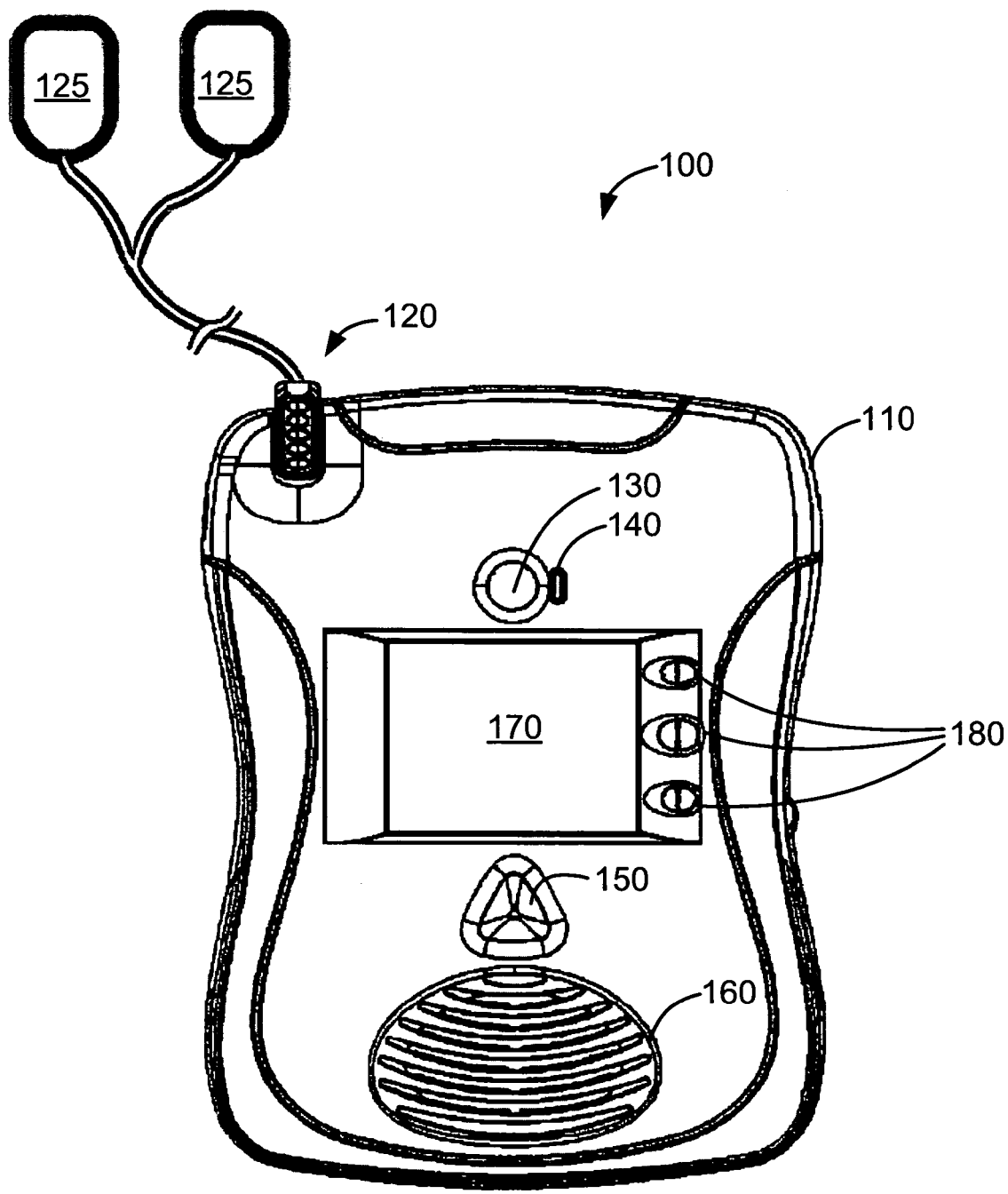
FIG. 1 illustrates a plan view of an AED according to one exemplary embodiment of the invention.

Turning now to the drawings, in which like reference numerals refer to like elements, FIG. 1 illustrates a plan view of an AED 100 with a built-in video display 170 according to one exemplary embodiment of the invention. The video display 170 may comprise any type of changeable visual presentation technology that is capable of displaying text or graphic (or both) output from a computer processor. For example, the video display may comprise liquid crystal display (LCD) technology, plasma displays, flat-screen display technology, three-dimensional or holographic technology, video projection technology, cathode ray tube (CRT) technology, and other similar display technology.

An operator may interact with the AED 100 and navigate through menu and graphical user interfaces on display 170 using a touch sensitive element, such as a touch screen 270, overlaying, or incorporated into, video display 170 when the AED is in a fully operative state such as during a rescue. Additionally, or in the alternative, an operator may interact with the AED 100 and navigate menu and graphical user interfaces on video display 170 using buttons 180.

According to one inventive aspect of the status indicating system, an operator of an AED 100 may obtain status information presented on the video display 170 of the AED 100 by pressing a single button or touching the touch screen 270 and without navigating through any menus on the video display 170 and while the AED 100 is in an non-operative state. A non-operative state of the AED 100 usually includes situations in which an AED 100 is not performing a rescue on a patient. To obtain this standby status information on the video display 170, an operator can touch the display 170 or one of the buttons 180 that may be designated as a "status information" button.

The standby processor and related circuitry is not illustrated in FIG. 1, but is contained within a housing 110 of the AED 100. On/off button 130 may be used by an operator to switch AED 100 between operational mode and standby mode. While the on/off button appears to the user to turn off AED 100 completely, the AED may actually be placed into a standby mode or non-operative state where the main processor may be powered off and a very low power standby processor may be operating to monitor activation of the touch screen of the display or the designated status information button of the buttons 180.

During standby operation, the standby processor (not illustrated in FIG. 1) may power up the main processor only to perform periodic tests of AED 100 such as memory, charging circuits, and battery power level. During the periodic tests, the standby processor can power up the main processor for only performing these self tests without the entire AED entering into a fully operational state. In other alternative embodiments, the standby processor could perform these self tests without using the main processor.

During standby operation, the standby processor may also use indicator light 140 to display overall system status, such as green illumination if all system tests pass or red illumination if AED 100 requires attention due to a system test failure or a low battery warning. The standby processor may also audibly or aurally indicate the status of the AED 100 using speaker 160. For example, the standby processor may chirp the speaker 160 when operator attention is required.

According to an alternate exemplary embodiment, the speaker 160 can be used for presenting oral or audible status information in addition, or in the alternative, to presenting status information on the video display 170. It is envisioned that some AEDs 100 may not have a video display 170 but will usually have a speaker 160. In such embodiments, oral or audible status indication can be provided with the speaker 160 in which the main processor 220 will supply appropriate audio signals that convey status information of the AED 100, similar to the information that would be conveyed with the video display 170.

To obtain status information from an the AED 100, an operator can obtain such status information by depressing one or more of buttons 180. The standby processor may detect this request and activate the main processor 220 for only displaying a status report on video display 170 or presenting audio signals to the speaker 160 that convey status of the AED 100.

While AED 100 is in standby mode, the standby processor may detect that the operator has depressed on/off button 130. At this time, the standby processor may power on the main processor of AED 100 placing the system in full operational mode, as in a rescue for a patient. In full operational mode, patient electrodes 125, which may attach to AED 100 via connector 120, can be used to monitor ECG information from a patient to determine if the patient's cardiac rhythm is suitable for defibrillation shock. If so, the operator may be instructed to press shock button 150 to initiate an electrical shock through the patient electrodes 125 attached at connector 120. During this procedure, ECG information may be displayed on video display 170. Video display 170, along with speaker 160, may also be used to present real-time instructions and feedback to the operator.

Figure 2:
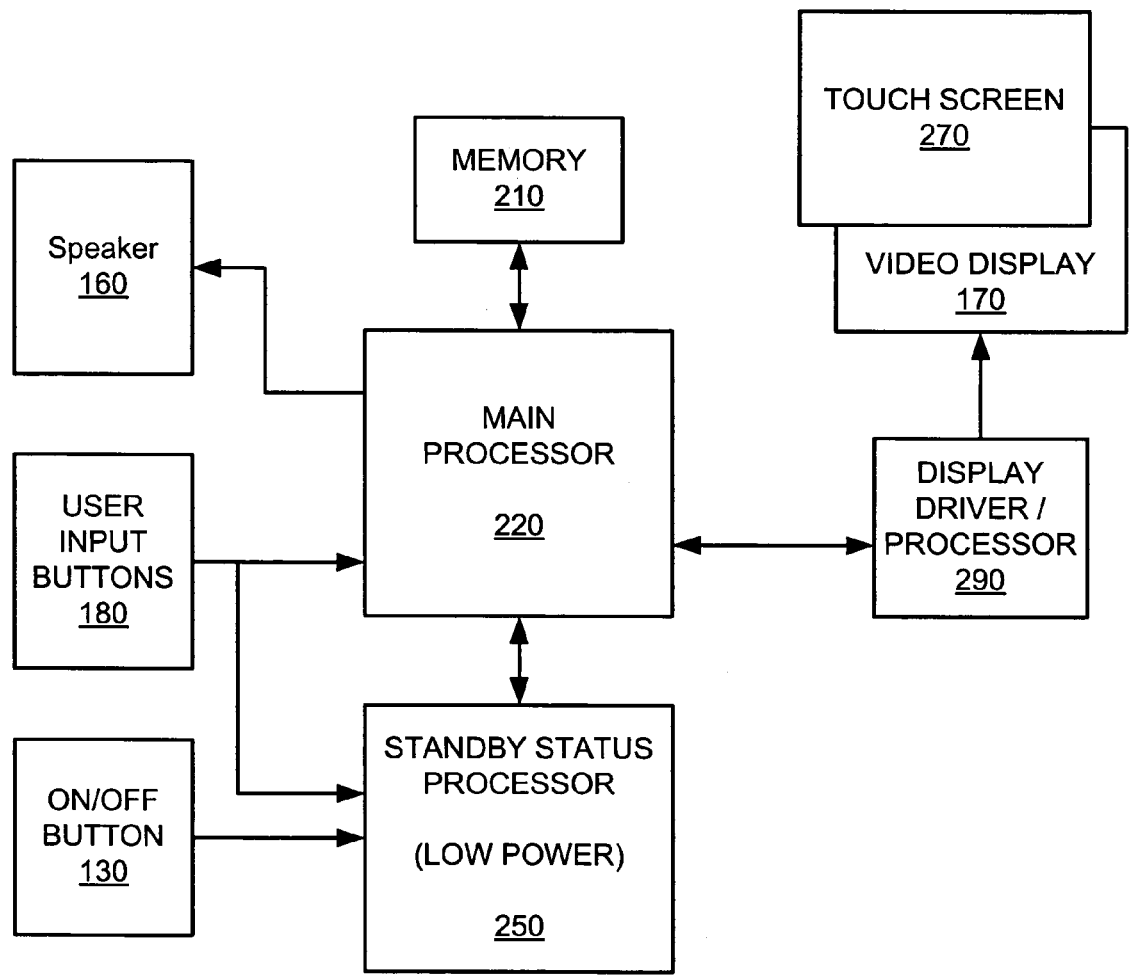
FIG. 2 is a functional block diagram illustrating the main processor, standby status processor, and user interface elements according to one exemplary embodiment of the invention.

Referring now to FIG. 2, this figure illustrates a functional block diagram of the processors and user interface elements according to one exemplary embodiment of the invention. In this exemplary embodiment, a standby processor 250 may accept user inputs, perform system tests by powering up the main processor 220, or activating the main processor 220 to display status information without placing the entire AED 100 into a fully operational state. While AED 100 is in standby mode, the standby processor 250 may accept user inputs from buttons 180, on/off button 130 and touch screen 270. An operator may request the display of status information by depressing one or more of user input buttons 180. The standby processor 250 may detect a status request and activate the main processor 220 to only display a status report on video display 170. This display of status information about the AED may be performed by the low power standby processor 250 activating the main processor 220 and without placing the entire AED 100 into a fully operational state.

While AED 100 is in standby mode, standby processor 250 may detect that the operator has depressed on/off button 130. At this time, standby processor 250 may power on main processor 220 of AED 100 placing the system in operational mode. While on/off button 130 can be used by the standby processor 250 to power main processor 220 on and off, the other user interface buttons 180 and touch screen 170 may be used by both the standby processor 250 and the main processor 220. For example, display driver 290, which can drive video display 170, may be addressed in standby mode by the main processor 220 for displaying standby status information. In full operational mode, main processor 220 can communicate with the display driver/processor 290 for displaying ECGs; operator instructions; menus; or other operational information, images, or video. Likewise, user inputs from buttons 180 or touch sensitive element 270 may be monitored by both main processor 220 and standby processor 250.

According to one exemplary embodiment of the invention, standby processor 250 may comprise a general purpose processor such as the MSP430F1232, an ultra-low-power microcontroller, made by Texas Instruments. However, one of ordinary skill in the art will appreciate that standby processor 250 may comprise a microcontroller, microprocessor, DSP processor, application specific logic, programmable logic, or numerous other forms without departing from the spirit and scope of the invention.

Main processor 220 may comprise a general purpose processor but it may not be as lower power relative to the standby processor 250. The main processor 220 communicates with the display driver/processor 290. The display driver/processor 290 may comprise a video processor that has the sole function of controlling the operation of the video display 170. While the display driver/processor 290 is illustrated as a separate physical component relative to the main processor 220, one of ordinary skill in the art recognizes that the display driver 290 could be part of the main processor 220 in other alternative embodiments (not illustrated). Similarly, though not illustrated, the standby processor 250 could form a part of the main processor 220. That is, it is envisioned that the main processor 220 in future embodiments could comprise a low power, sleep mode similar to the one of the standby processor 250.

Meanwhile, memory 210 is illustrated as separate from, and could be shared by, both standby processor 250 and main processor 220. However, one of ordinary skill in the art will appreciate that each processor 220, 250 may have its own internal or external memory where each memory may be volatile, nonvolatile, or a combination thereof. These memories may or may not be shared between the two processors. Further, one or more memory ports (not illustrated) that are positioned on the outside of the housing for the AED 100 may be used for receiving one or more removable, portable memory devices, such as memory cards (not illustrated). The main processor 220 or the standby processor 250 (or both) may read or write (or both) to the memory devices (not illustrated).

Figure 3:
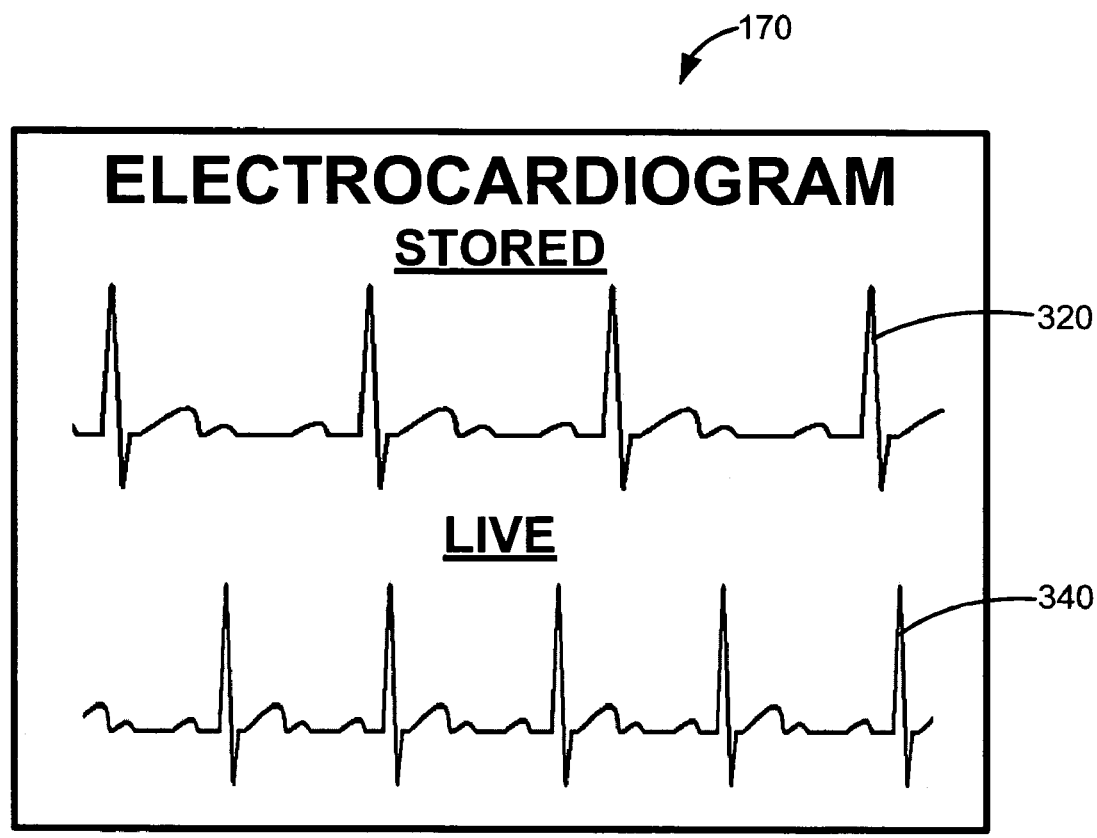
FIG. 3 illustrates an AED video screen displaying an electrocardiogram according to one exemplary embodiment of the invention.

Referring now to FIG. 3, this figure illustrates an AED video display 170 for presenting an electrocardiogram (ECG) when the AED 100 is in a full operational mode according to one exemplary embodiment of the invention. During full operational mode, such as during a rescue, main processor 220 may be active. While in an active state, main processor 220 may provide information to present on video display 170 including patient ECG waveforms. AED 100 may display live EGG waveforms 340 from a patient on video display 170. AED 100 may also display recorded waveforms 320 that are stored in memory 210. Waveforms 320 stored in memory 210 may be useful in reviewing a rescue event or for training an AED operator.

Figure 4:
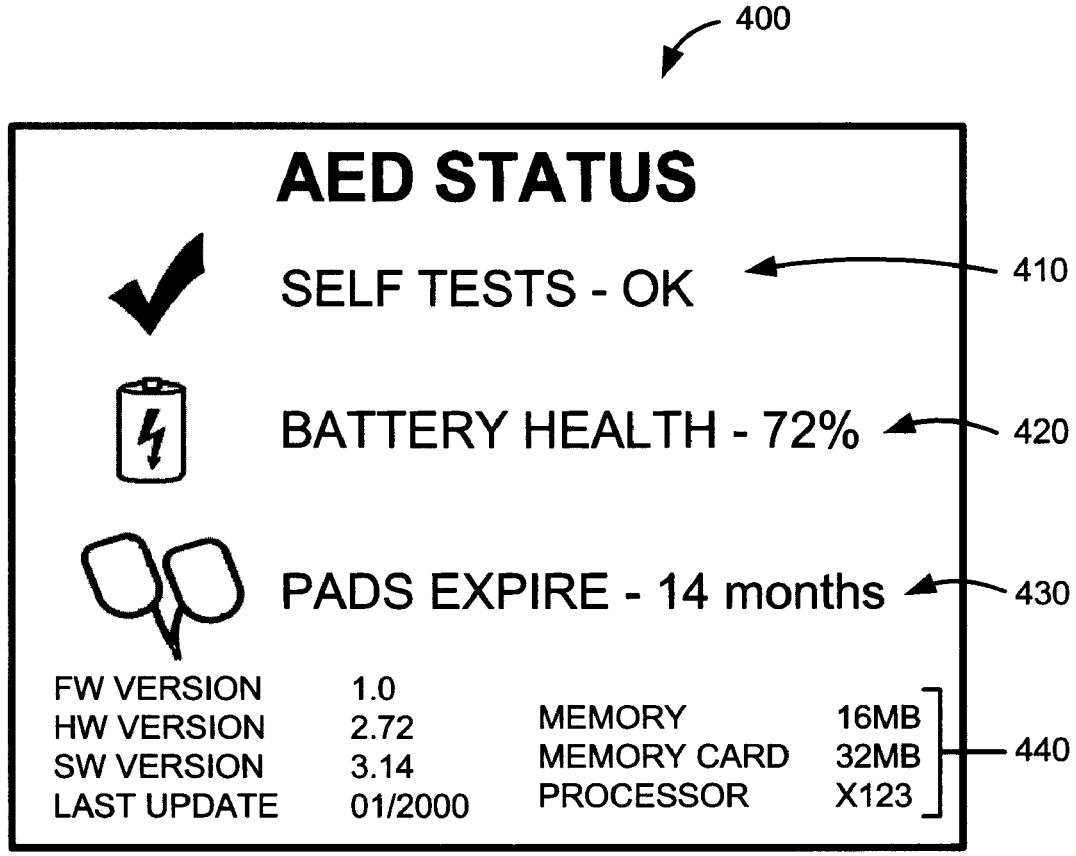
FIG. 4 illustrates an AED video screen displaying status information according to one exemplary embodiment of the invention.

Referring now to FIG. 4, this figure illustrates video display 170 for presenting status information 400 according to one exemplary embodiment of the invention. Standby processor 250 can respond to an operator's request to display the status of AED 100 by presenting system status information 400 on video display 170. The status information may comprise information such as self test results 410, battery status 420, patient electrode pad expiration date 430, the presence or non-presence of electrode pads, or various other system information 440 such as software or firmware (or both) version numbers and memory capacities.

Standby processor 250 may display this status information screen on video display 170 by activating the main processor 220 and without placing the entire AED 100 into a full operational mode. During a full operational mode, such as during a rescue, main processor 220 can control the display processor 290 to present rescue information such as ECG waveforms 320, 340 or other rescue information as illustrated in FIG. 4.

Figure 5:
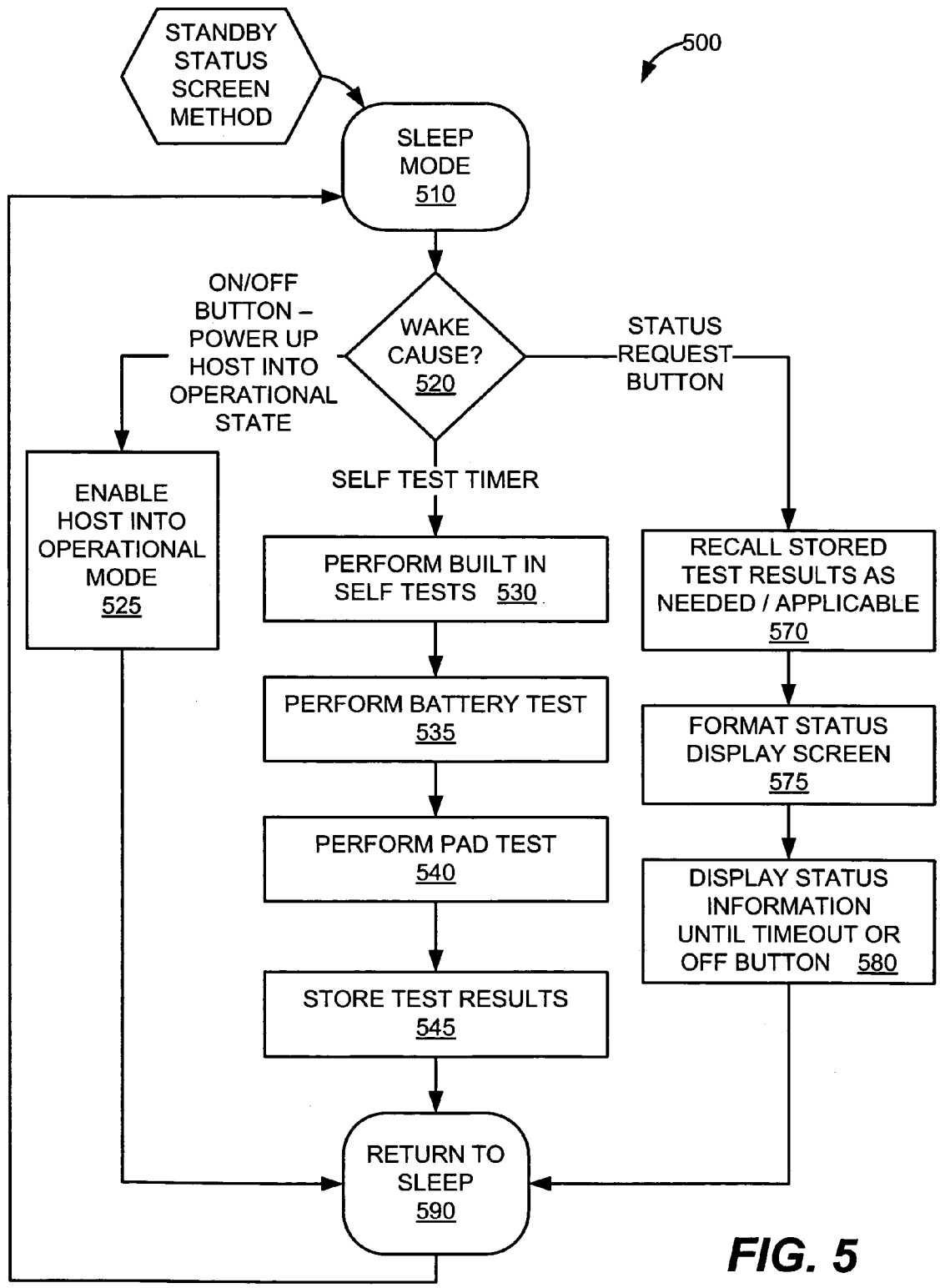
FIG. 5 is a logic flow diagram highlighting exemplary steps for an AED using a video display to present standby status information to a user according to one exemplary embodiment of the invention.

FIG. 5 illustrates a logic flow diagram 500 of a method for presenting standby status information on a video display 170 according to one exemplary embodiment of the invention. Logical flow diagram 500 highlights some key functional features of standby processor 250. One of ordinary skill in the art will appreciate that process functions of standby processor 250 may comprise firmware code executing on a microcontroller, microprocessor, or DSP processor; state machines implemented in application specific or programmable logic; or numerous other forms without departing from the spirit and scope of the invention. In other words, the invention may be provided as a computer program which may include at machine-readable medium having stored thereon instructions which may be used to program a computer (or other electronic devices) to perform a process according to the invention.

The machine-readable medium: may include, but is not limited to, floppy diskettes, optical disks, CD-ROMs, and magneto-optical disks, ROMs, RAMs, EPROMs, EEPROMs, magnet or optical cards, flash memory, or other type of media/machine-readable medium suitable for storing electronic instructions.

Certain steps in the processes or process flow described in all of the logic flow diagrams referred to below must naturally precede others for the invention to function as described. However, the invention is not limited to the order or number of the steps described if such order/sequence or number does not alter the functionality of the present invention. That is, it is recognized that some steps may not be performed, while additional steps may be added, or that some steps may be performed before, after, or in parallel other steps without departing from the scope and spirit of the present invention.

Further, one of ordinary skill in programming would be able to write such a computer program or identify the appropriate hardware circuits to implement the disclosed invention without difficulty based on the flow charts and associated description in the application text, for example. Therefore, disclosure of a particular set of program code instructions or detailed hardware devices is not considered necessary for an adequate understanding of how to make and use the invention. The inventive functionality of the claimed computer implemented processes will be explained in more detail in the following description in conjunction with the Figures illustrating process flows.

Step 510 is the first step in the process and can comprise a waiting step. In this step, standby processor 250 operates in a power saving sleep mode and can be woken by events that it acts upon briefly before returning back to the sleep mode. In the exemplary embodiment of the method illustrated in FIG. 5, three events may activate standby processor 250 from its sleep mode. These events include, but are not limited to, a power button event, a self test timer event, or a status request event. After an event that takes standby processor 250 out of its sleep mode, the standby processor 250 can activate the main processor 220. Once the main processor 220 is activated, it can determine what type of event awoke the standby processor 250 from its sleep mode. The main processor 220 and standby processor 250 will eventually transition back through step 590 into the sleep mode of step 510 where standby processor 250 waits for the next wake event and the main processor 220 is deactivated or turned off completely to conserve power.

In decision step 520, standby processor 250 activates the main processor 220 to determine what type of event is occurring. If the wake event comprises a power button 130 being pressed, the process continues to step 525 in which the main processor 220 enters into a full operational mode such as for a rescue event. In full operational mode, main processor 220 is powered on to perform the main operations of AED 100. For example, main operations of the AED 100 can include patient heart rhythm analysis and possible delivery of defibrillation shocks to the patient. Once the main processor 220 is enabled, standby processor 250 transitions from step 525 into step 590 where standby processor 250 returns to sleep mode of step 510. Functions of standby processor 250 may occur in parallel to operational functions of main processor 220.

If the wake event determined in step 520 by the main processor 220 is a self test timer, the main processor 220 can perform periodic system tests starting with step 530 where built-in self tests are performed. In an alternate embodiment, not illustrated, the standby processor 250 could be designed to conduct these self tests alone and without using the main processor 250.

The self test timer can be internal to standby processor 250 or it may be a circuit (not illustrated) that is external to standby processor 250. An example of a period of the self test timer may be one day. According to this example, self tests would be performed once each day. One of ordinary skill in the art will appreciate that this timer period may differ from this example and may be a constant or vary according to other system parameters without departing from the scope and spirit of the present invention.

The self tests performed according to the self test timer may include the main processor 220 testing system memory 210, validating software/firmware, checking charging circuits, or other internal tests of AED 100. Next, standby processor 250 transitions to step 535 where battery tests are performed, and then to step 540 where patient electrode pads are tested. Then, in step 545, the results of these test functions may all be stored in the memory 210 of AED 100. Once self tests are completed, standby processor 250 transitions from storage step 545 into step 590 where standby processor 250 returns to sleep mode of step 510.

If the wake event determined in step 520 is an operator status request, the main processor 220 can communicate with the display driver/processor 290 to present AED system status on video display 170. This starts with collecting the system information to display. According to one exemplary aspect of the inventive status indicating system, the main processor 220 and standby processor 250 do not present any complex menus on the display 170 so that an operator of an AED can readily obtain status information about the AED 100 from a single press of a button 180 or activation of a touch screen 270 without navigating through complex menus and without the main processor 220 performing any time-consuming and power-consuming self tests. In the exemplary embodiment illustrated in FIG. 5, collecting information to display begins in step 570 in which information is usually recalled from memory 210 by main processor 220 based on a prior periodic test, as discussed above in step 545.

In step 575, information collected or recalled in step 570 may be formatted for presentation on video display 170. Finally, in step 580, the status information is displayed to the operator. This presentation of information on the display 170 may continue until a display timer expires or the operator presses one of buttons 180 again or touch screen 270. An example of the duration for the display can be between ten and thirty seconds. According to a preferred exemplary embodiment, the duration is ten seconds. One of ordinary skill in the art will appreciate that this duration for displaying status information may differ from this example and may be a constant or a variable length without departing from the scope and spirit of the present invention. At completion of the display of status information, standby processor 250 transitions from display step 580 into step 590 where standby processor 250 returns to the sleep mode of step 510.

Figure 6:
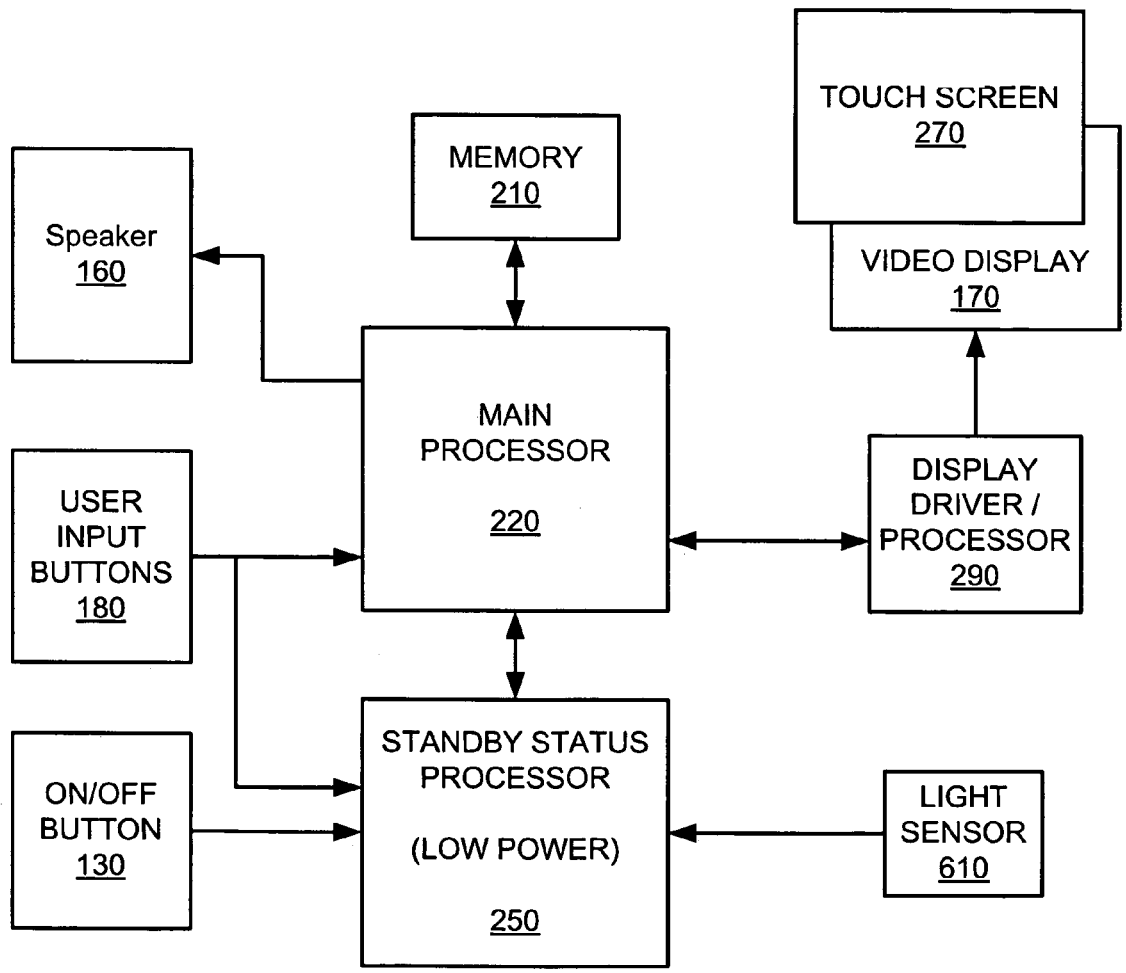
FIG. 6 is a functional block diagram illustrating the standby status processor, video display and a light sensor for detecting the ambient environment.

Referring now to FIG. 6, this figure illustrates a functional block diagram of the standby status processor, video display and a light sensor for detecting the ambient environment. Prior to requesting the main processor 220 to present status information on video display 170, standby processor 250 may sample light sensor 610 to determine the ambient light level around the AED 100.

Display driver 290 may control the intensity, brightness, and/or contrast of video display 170. Standby processor 250 can set these parameters within display driver 290 based on ambient light levels sampled from light sensor 610. The standby processor 250 can also store these parameters in memory 210 so that the main processor 220 can access them when it is in a full operative state, such as during a rescue. This environmentally responsive determination of display parameters may provide for a more readable video display 170. This feature may also conserve AED battery power, for example, by providing a dimmer display in a dark environment of the AED 100.

Alternative embodiments of the inventive system will become apparent to one of ordinary skill in the art to which the present invention pertains without departing from its spirit and scope. Thus, although this invention has been described in exemplary form with a certain degree of particularity, it should be understood that the present disclosure has been made only by way of example and that numerous changes in the details of construction and the combination and arrangement of parts or steps may be resorted to without departing from the spirit or scope of the invention. Accordingly, the scope of the present invention is defined by the appended claims rather than the foregoing description.

What is claimed is:

1. A defibrillator system, comprising:
a defibrillator having programmable circuitry, the programmable circuitry including a video display and having a user "on" state and a user "off" state, the user "on" state comprising an initiation of a rescue; and
a user interface for activating the programmable circuitry in the user "off" state to send status information to the video display, wherein the status information can be obtained from the defibrillator without placing the defibrillator in the user "on" state.

2. The defibrillator system of claim 1, wherein the status information comprises one of self test results, battery health, patient electrode pad information, software version number, firmware version number, and memory capacity.

3. The defibrillator system of claim 1, further comprising an on/off button, the on/off button switching the defibrillator between the "on" state and the "off" state.

4. The defibrillator system of claim 1, wherein the user interface comprises one of a button and a touch screen display.

5. The defibrillator system of claim 1, wherein the programmable circuitry comprises a standby status processor and a main processor, the standby status processor controlling activation of the main processor, and the main processor functioning in both the user "off" state and the user "on" state.

6. The defibrillator system of claim 1, wherein the defibrillator is portable.

7. The defibrillator system of claim 1, wherein the display supports full motion video when the defibrillator is in the user "on" state.

8. The defibrillator system of claim 1, wherein the status information is stored in a memory electrically connected to the programmable circuitry prior to activating the programmable circuitry to send the status information to the video display.

9. The defibrillator system of claim 1, wherein the status information comprises text or symbols.

10. A method for displaying status information on a video display of a defibrillator, comprising:
providing a defibrillator having a user "on" state and a user "off" state, the user "on" state comprising an initiation of a rescue;
with the defibrillator in the user "off" state, instructing the defibrillator to send defibrillator status information to a video display;
sending defibrillator status information to a video display while the defibrillator is in the user "off" state; and
displaying the defibrillator status information on the video display while the defibrillator is in the user "off" state, wherein the defibrillator status information can be obtained from the defibrillator without placing the defibrillator in the user "on" state.

11. The method of claim 10, further comprising discontinuing display of the status information in response to one of expiration of a time period and a signal from a user interface.

12. The method of claim 10, further comprising performing self tests on the defibrillator, wherein the status information contains self-test results.

13. The method of claim 12, further comprising displaying defibrillator status information that comprises text or symbols.

14. The method of claim 10, further comprising reading electrode pad information comprising an expiration date from a patient electrode pad, wherein the status information comprises the electrode pad information.

15. The method of claim 10, further comprising reading electrode pad information regarding information about a state of a patient electrode pad coupled to the defibrillator, and wherein the status information comprises the electrode pad information.

16. The method of claim 10, further comprising storing status information including self-test results, the stored status information being sent to the video display.

17. The method of claim 10, wherein instructing the defibrillator to send status information comprises using a button and a touch screen display.

18. A method for displaying status information of a defibrillator, comprising:

providing a defibrillator having a user "on" state and a user "off" state, the user "on" state being associated with an initiation of a rescue;

with the defibrillator in the user "off" state, recalling stored results of defibrillator self-tests from memory; and displaying the stored results on a video display with the defibrillator in the user "off" state, wherein the stored results can be obtained from the defibrillator without placing the defibrillator in the user "on" state.

19. The method of claim 18, further comprising displaying defibrillator status information while in the user "off" state that comprises intelligible text or symbols.

20. The method of claim 18, further comprising discontinuing display of the stored results in response to one of expiration of a time period and a signal from a user interface.

21. The method of claim 18, further comprising displaying defibrillator status information that comprises displaying one of battery health, patient electrode pad information, software version number, firmware version number, and memory capacity.

22. A method for displaying status information on a video display of a host device, comprising:

providing a host device having a user "on" state that comprises a rescue operation state and a user "off" state;

sending status information to a video display coupled to the host device while the host device is in the user "off" state; and displaying the status information on the video display while the host device is in the user "off" state, wherein the status information can be obtained from the host device without placing the host device in the user "on" state.

23. The method of claim 22, further comprising activating a button of the host device to send status information to the video display, wherein the host device is a defibrillator.

24. The method of claim 22, further comprising discontinuing display of the status information in response to one of expiration of a time period and a signal from a user interface.

25. The method of claim 22, further comprising activating a button of the host device to send status information to the video display.

26. The method of claim 22, further comprising performing self tests on the host device, wherein the status information comprises results of the self tests.

* * * * *